United States Patent
Brewer et al.

(10) Patent No.: US 8,715,233 B2
(45) Date of Patent: May 6, 2014

(54) ASSISTIVE METHOD AND VISUAL-AID DEVICE FOR VASCULAR NEEDLE INSERTION

(71) Applicant: The Board of Trustees of The Leland Stanford Junior University, Palo Alto, CA (US)

(72) Inventors: Reuben Daniel Brewer, Millbrae, CA (US); J. Kenneth Salisbury, Jr., Mountain View, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 19 days.

(21) Appl. No.: 13/725,781

(22) Filed: Dec. 21, 2012

(65) Prior Publication Data

US 2013/0184680 A1    Jul. 18, 2013

Related U.S. Application Data

(60) Provisional application No. 61/578,841, filed on Dec. 21, 2011.

(51) Int. Cl.
| | | |
|---|---|---|
| *A61B 18/14* | (2006.01) | |
| *A61B 5/00* | (2006.01) | |
| *A61M 25/06* | (2006.01) | |
| *A61B 5/06* | (2006.01) | |
| *A61B 17/34* | (2006.01) | |
| *A61B 19/00* | (2006.01) | |

(52) U.S. Cl.
CPC .......... *A61B 5/0059* (2013.01); *A61M 25/0693* (2013.01); *A61B 5/06* (2013.01); *A61B 17/3403* (2013.01); *A61B 2019/5445* (2013.01)
USPC ....................... 604/116; 600/424; 604/168.01

(58) Field of Classification Search
CPC ... A61M 25/0693; A61B 5/0059; A61B 5/06; A61B 17/3403; A61B 2019/5445
USPC .......... 600/178, 179, 182, 424, 476; 604/116, 604/168.01, 510
See application file for complete search history.

(56) References Cited

U.S. PATENT DOCUMENTS

| 8,376,978 B2 * | 2/2013 | Roger et al. ................. 604/4.01 |
| 2005/0070788 A1 * | 3/2005 | Wilson et al. ................. 600/424 |
| 2007/0088279 A1 * | 4/2007 | Shue et al. ............... 604/168.01 |
| 2008/0177174 A1 * | 7/2008 | Crane ........................... 600/424 |
| 2008/0194973 A1 * | 8/2008 | Imam ............................. 600/478 |
| 2008/0195060 A1 * | 8/2008 | Roger et al. .................. 604/246 |
| 2012/0101440 A1 * | 4/2012 | Kamen et al. ............. 604/164.08 |
| 2013/0006178 A1 * | 1/2013 | Pinho et al. ................... 604/116 |

* cited by examiner

*Primary Examiner* — Nicholas Lucchesi
*Assistant Examiner* — Gerald Landry, II
(74) *Attorney, Agent, or Firm* — Shay Glenn LLP

(57) ABSTRACT

A vascular access device is provided with a needle assembly, a catheter assembly configured to slidably receive the needle assembly, and a light emitting assembly configured to couple to the needle assembly. The light emitting assembly and the needle assembly cooperate to shine a beam of light down the bore of the needle to assist with aligning the needle with a penetration site on target tissue. Systems and methods associated with these devices are also disclosed.

18 Claims, 8 Drawing Sheets

ASSISTIVE METHOD AND VISUAL-AID DEVICE FOR VASCULAR NEEDLE INSERTION

CROSS REFERENCE TO RELATED APPLICATIONS

This patent application claims priority to provisional patent application Ser. No. 61/578,841, filed on Dec. 21, 2011 and titled "ASSISTIVE METHOD AND VISUAL-AID DEVICE FOR VASCULAR NEEDLE INSERTION."

INCORPORATION BY REFERENCE

All publications and patent applications mentioned in this specification are herein incorporated by reference to the same extent as if each individual publication or patent application was specifically and individually indicated to be incorporated by reference.

FIELD

The present invention generally relates to vascular access, and more particularly to systems, devices and methods for aligning a needle with a tissue insertion site.

BACKGROUND

Vascular access includes any procedure wherein a needle is used to puncture a vein or artery. The most common forms of vascular access are intravenous (IV) catheter insertion for the delivery of fluids, phlebotomy sticks for extracting venous blood samples, and arterial sticks for extracting arterial blood samples. There are two main difficulties in vascular access: locating the vein or artery and precisely aiming and moving the needle into the vessel.

Locating veins and arteries is often difficult because they sit beneath layers of skin and fat. In healthy men and many elderly patients, veins can be seen and felt readily at common insertion locations such as the hands and arms. However, many women and children do not have easily-locatable veins. Arteries are located deeper than veins and cannot be seen with the naked eye. However, some arteries can be located very roughly through palpating for the patient's pulse. Infrared (IR) light can be used to see veins and arteries because blood absorbs IR light much more readily than do the tissues that surround the vessels targeted for vascular access. Accordingly, an infrared picture of a vein or artery shows the vessel as dark on a light background.

Precisely aiming and moving a small needle into a vein or artery that is not much bigger than the needle can be challenging, particularly in smaller patients such as infants and children. Aligning the needle at the desired initial angles and insertion point can typically be half of the problem. To obtain an accurate estimate of the insertion point, the needle tip must be kept close to the surface of the skin. However, a small, aberrant motion could nick the skin and injure the patient. Even a small nick could produce enough blood to obscure the insertion point for a considerable time while the nick clots, or can cause local vasoconstriction (shrinking) of the surrounding vessels, making insertion much more difficult. However, keeping the needle tip at a larger, safer distance from the skin while aligning the needle provides a less accurate visual estimate of the insertion point, increasing the chances of missing the targeted vessel.

What is needed and is not provided by the prior art are methods and devices for assisting medical practitioners with locating access points in veins and arteries, and for assisting practitioners with safely and precisely aiming an access needle at the insertion point with a desired needle trajectory during vascular access.

SUMMARY OF THE DISCLOSURE

The present invention relates to methods and devices configured to assist medical practitioners with insertion of a vascular access needle. According to aspects of the invention, a laser may be shown directly down the bore of a hollow needle to facilitate aiming of the needle in vascular access procedures, including the placement of IV catheters, phlebotomy sticks, and arterial sticks. The laser shows where on the skin the needle will penetrate along its current orientation so that the needle's alignment can be adjusted at a further, safer distance to the skin than would be possible without the laser. In some embodiments, the device includes an optically clear filter that attaches to the end of a needle such that the needle's sterility and normal operation are maintained while allowing for a laser to pass through it. According to aspects of the invention, the device includes a novel configuration for aligning the laser beam with the needle bore both in translation and rotation. In some embodiments, such a laser-aimed needle may be located on a linear slide with a C-arm arrangement so that the needle can be moved easily to penetrate the skin exactly where the laser is aimed.

According to one embodiment, a visual-aid device for vascular needle insertion is provided with a needle, a flexible catheter, a flash chamber, a filter, and a light emitting assembly. The needle includes a proximal end, a sharp distal end, and a lumen extending between the proximal and distal ends. The catheter has a lumen configured to receive the distal end of the needle therethrough. The flash chamber is located at the proximal end of the needle and is in fluid communication with the needle lumen. The flash chamber comprises a non-opaque portion configured to permit visualization of a body fluid located inside the chamber from outside of the chamber. The filter is attached to the flash chamber and has a proximal side and a distal side. The distal side of the filter is located in fluid communication with the inside of the flash chamber and the proximal side is located in fluid communication with the outside of the flash chamber. The filter is configured to allow air to pass therethrough and to prevent or inhibit liquid from passing therethrough. The light emitting assembly has an output optically coupled to the needle such that light from the light emitting assembly can travel from the proximal end of the needle through the distal end of the needle to project a visible spot on an object adjacent to the distal end of the needle when the filter is attached to the flash chamber.

Methods of visually aiding vascular needle insertion are also provided.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The two basic types of vascular access are venous and arterial, with venous being the most commonly used. Intravenous (IV) access can be further classified as central (into veins located inside the chest or abdomen), or peripheral (veins located peripherally from the chest and abdomen). (http://en.wikipedia.org/wiki/Intravenous_therapy). Peripheral venous access is the most common access method used in both hospitals and pre-hospital services, and can be used to draw blood and/or deliver fluids to the vein. A peripheral IV line typically consists of a short catheter (a few centimeters long) inserted through the skin into a peripheral vein. This is usually in the form of a cannula-over-needle device, in which a flexible plastic cannula comes mounted on a metal trocar or needle. Once the tip of the needle and cannula are located in the vein the trocar is withdrawn and discarded and the cannula advanced inside the vein to the appropriate position and secured. Any accessible vein can be used although arm and hand veins are used most commonly, with leg and foot veins used to a much lesser extent. In infants the scalp veins are sometimes used.

The part of the catheter that remains outside the skin is called the connecting hub. The connecting hub is typically provided with a Luer lock fitting that allows the hub to be connected to a syringe or an intravenous infusion line, or capped with a bung between treatments. Ported cannulae have an injection port on the top that is often used to administer medicine.

Existing catheter assemblies commonly include a "flash chamber" equipped with a filter. When the catheter and needle are first inserted, a small amount of blood flows up the needle from the vein and into the flash chamber to provide a visual indication to the medical practitioner that fluid communication has been established between the distal tip of the catheter assembly and the interior lumen of the vein. The filter allows air inside the needle and flash chamber to escape so that the flash blood can displace it, but the filter prevents blood from flowing through it, thereby preventing blood from flowing past the flash chamber.

Figure 1:
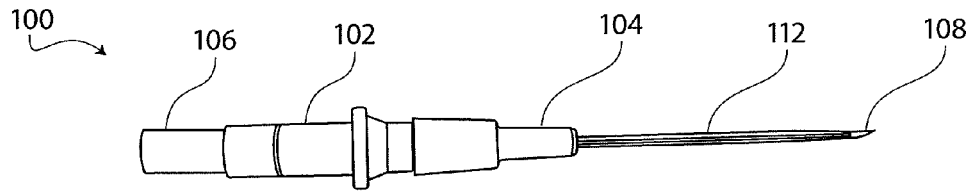
FIG. 1 is a plan view showing an exemplary catheter assembly constructed according to aspects of the invention.
Figure 2:
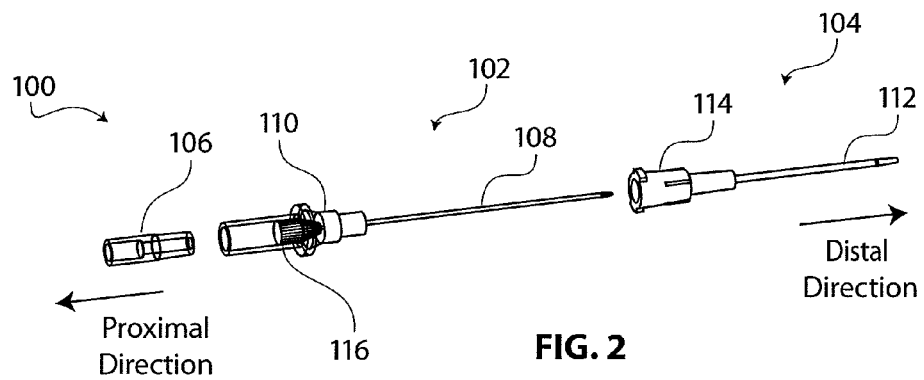
FIG. 2 is an exploded perspective view of the exemplary catheter assembly of FIG. 1.

Referring to FIGS. 1 and 2, an IV needle and catheter assembly 100 constructed according to aspects of the present invention is shown. This exemplary assembly includes a needle assembly 102, a catheter assembly 104, and a filter plug assembly 106. Needle assembly 102 includes a needle 108 and a plastic needle holder 110 formed on the proximal end of needle 108. Needle 108 is a hollow, metal tube with a sharp, beveled tip on its distal end for penetrating the skin and vein. Catheter assembly 104 includes catheter 112 and a plastic catheter holder 114 formed on the proximal end of catheter 112. Catheter 112 is a very thin tube made of a flexible, biocompatible plastic and is configured to slide over needle 108. Catheter assembly 104 is configured to slidably receive needle assembly 102 such that when the distal end of needle holder 110 nests inside catheter holder 114, the distal tip of needle 108 protrudes slightly from the distal end of catheter 112, as best seen in FIGS. 1 and 4.

Catheter holder 114 includes a Luer Lock screw thread, or "hub" on its proximal end that allows for IV bags to be attached to catheter assembly 104 (after needle assembly 102 has been removed) for the introduction of fluids, or for a syringe to be attached for the extraction of fluids. During insertion, catheter 112 and needle 108 move in unison to penetrate the skin and vein wall. However, the catheter's reach ends before the needle bevel so that the needle bevel can penetrate without damaging the delicate catheter tip. A flash chamber 116 is located on the proximal end of needle holder 110. As previously mentioned, flash chamber 116 is a translucent space where blood (or other fluid to be extracted) can pool and be seen through the side of needle holder 110. Filter plug 106 presses into the back of needle holder 110 and contains an air-permeable, blood-impermeable filter to allow the air to escape but trap the blood. In other embodiments (not shown), the filter plug can be integrally formed with the flash chamber.

Figure 3:
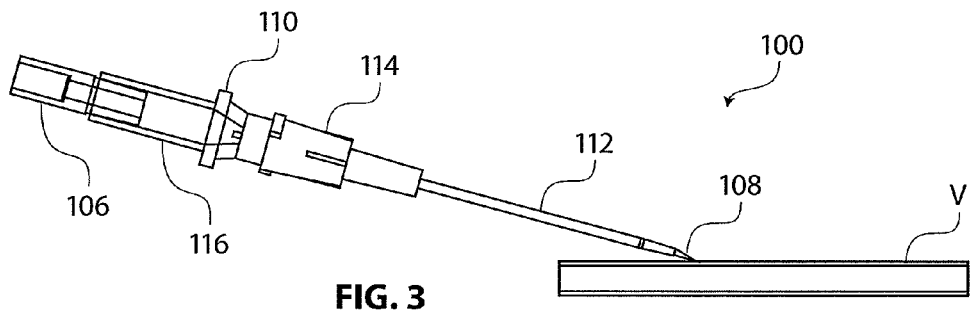
FIG. 3 is a side view schematically showing the exemplary catheter assembly positioned above a vein before penetration of the vein.
Figure 4:
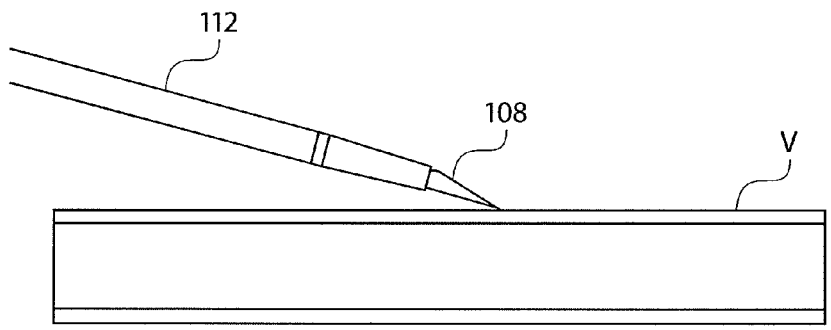
FIG. 4 is an enlarged side view schematically showing the distal tip of the exemplary catheter assembly before penetration of the vein.
Figure 5:
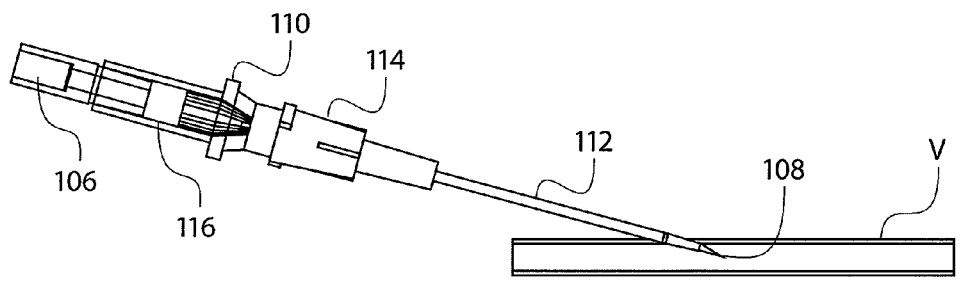
FIG. 5 is a side view schematically showing the needle and catheter just after penetration of the vein.
Figure 6:
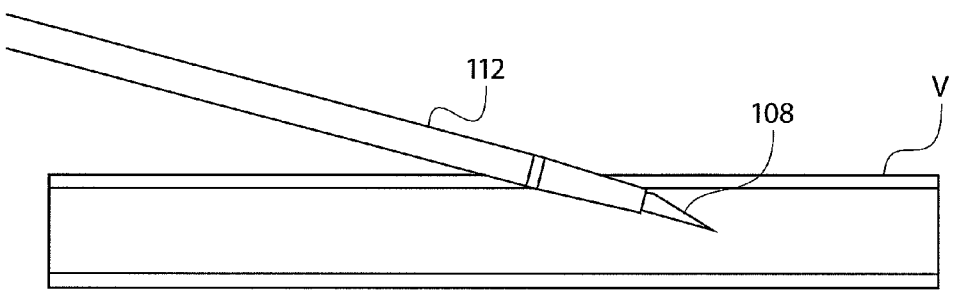
FIG. 6 is an enlarged side view schematically showing the needle and catheter just after penetration of the vein.
Figure 7:
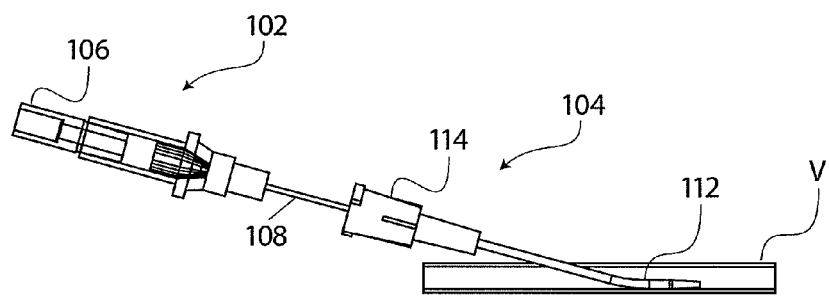
FIG. 7 is a side view schematically showing the catheter slid off of the needle and into the vein with the needle held stationary.
Figure 8:
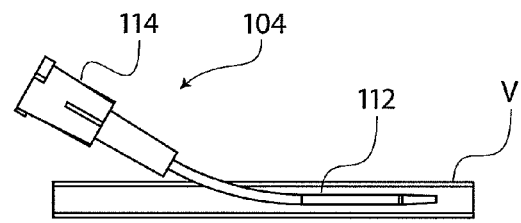
FIG. 8 is a side view schematically showing the catheter in place in the vein with the needle removed.

Immediately before insertion, as depicted in FIGS. 3 and 4, catheter 112 rides along needle 108, and the needle/catheter assembly 100 is held roughly 15 degrees or lower to the skin surface. The needle/catheter assembly 100 is typically moved so that the tip moves generally in a straight line while the assembly 100 is rotated progressively flatter against the hand. The needle penetrates first the skin and then the proximal wall of vein V. As needle 108 penetrates the proximal vein wall, as shown in FIGS. 5 and 6, blood enters needle 108 and fills the flash-chamber 116. Because the catheter's tip does not extend to the needle bevel, the assembly 100 is pushed a small distance beyond the point at which blood "flash" occurred to allow the distal tip of catheter 112 to enter the vein V. The distal tip of catheter 112 may be provided with a slight taper, as best seen in FIG. 4, to assist with the entry of catheter 112 into the vein. As the edge of the catheter tip is pushed beyond the edge of the hole created by needle 108, the axial resistance force on needle 108 decreases suddenly. The practitioner can usually feel this sudden force decrease, or "pop". Because the distance between the needle bevel and catheter tip is small and the insertion speed proportionately high, the practitioner often sees the blood flash and feels the force "pop" simultaneously. These two sensory cues are the main methods of verifying successful insertion of the catheter 112. Once the practitioner has observed from these sensory cues that the catheter tip is in the vein, the rest of catheter 112 is inserted, as shown in FIG. 7, while needle 108 is held stationary as a guide wire that prevents catheter 112 from buckling. Once catheter 112 has been fully inserted such that catheter holder 114 or the "hub" is adjacent the skin, needle 108 is withdrawn, as shown in FIG. 8. The medical practitioner temporarily applies finger pressure on vein V near the distal end of catheter 112 to prevent blood from flowing out of catheter holder 114 while needle assembly 102 is withdrawn and before an IV line is coupled to catheter holder 114.

As previously mentioned, a practitioner needs to verify that needle 108 and catheter 112 have been successfully inserted before collecting samples or administering fluids. In the most benign case, the mistaken usage of a failed vascular access site would be an annoying waste of time. In the case that life-saving medications must be administered or life-saving test samples extracted, the resulting delay could have dire consequences. The blood "flash" is one of the main verifications of a successful insertion. To obtain a blood "flash", the blood entering through the tip of needle 108 needs to push the air out the open proximal end of needle 108. However, sterility demands that the blood that enters needle 108 be trapped and not exit the needle with the air. To effect these two objectives, filter plug 106 is provided with a filter material that is air-permeable and blood-impermeable. Filter plug 106 also includes an optically transparent or translucent center portion, as will now be discussed in more detail. Standard, commercially-available IV catheters have a filter material that is opaque such that a laser could not be shone through it.

Figure 9:
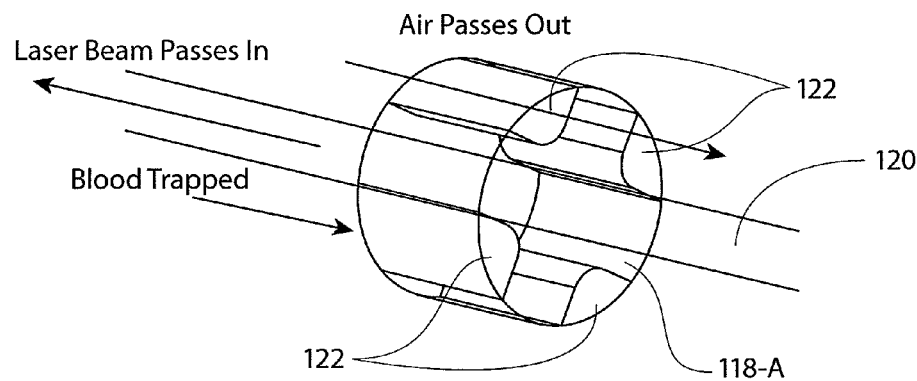
FIG. 9 is an enlarged perspective view depicting the operation of an exemplary filter constructed according to aspects of the invention.
Figure 10:
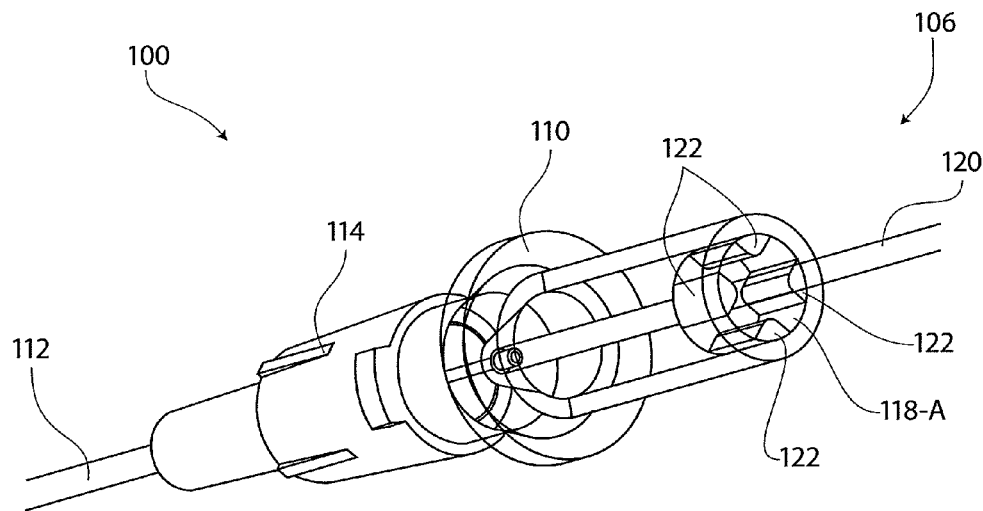
FIG. 10 is a perspective view showing the exemplary filter in place within the proximal end of the exemplary needle holder.
Figure 11:
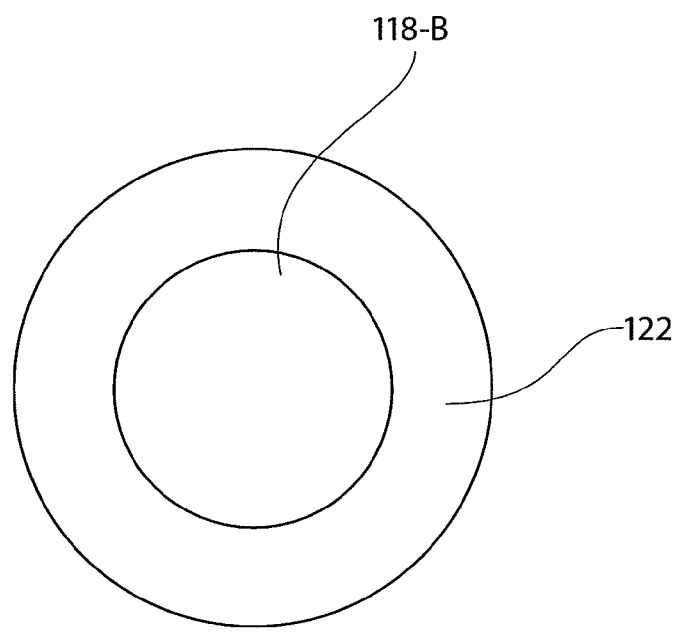
FIG. 11 is an end view showing an example of an annular filter.
Figure 12:
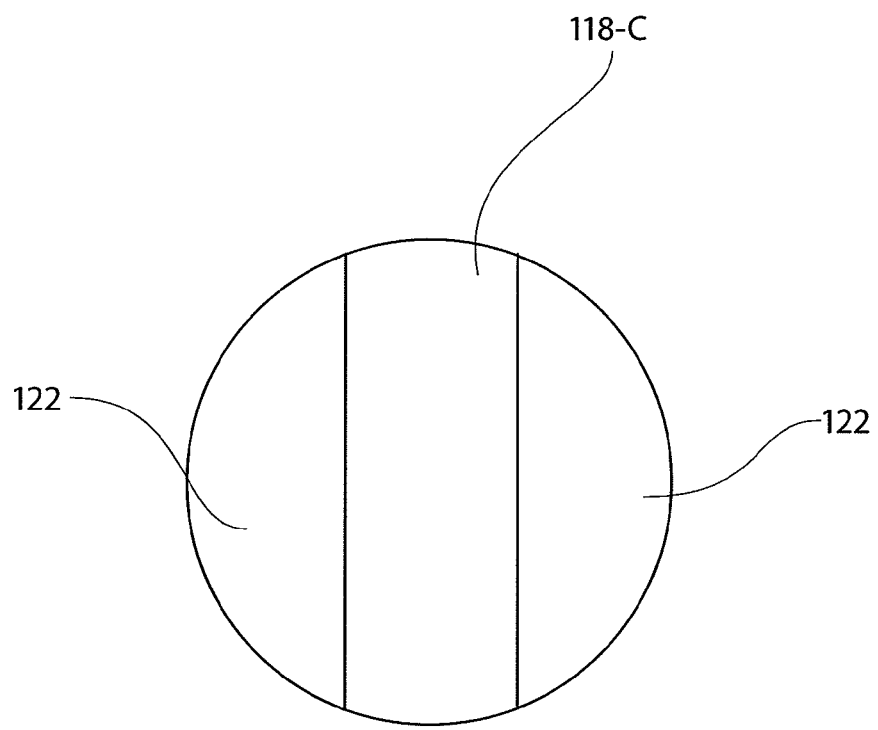
FIG. 12 is an end view showing an example of a two-prong filter.
Figure 13:
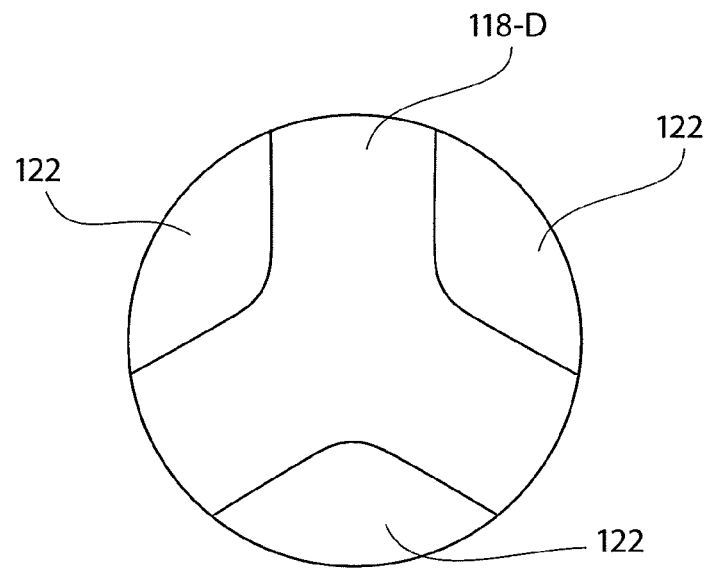
FIG. 13 is an end view showing an example of a three-prong filter.
Figure 14:
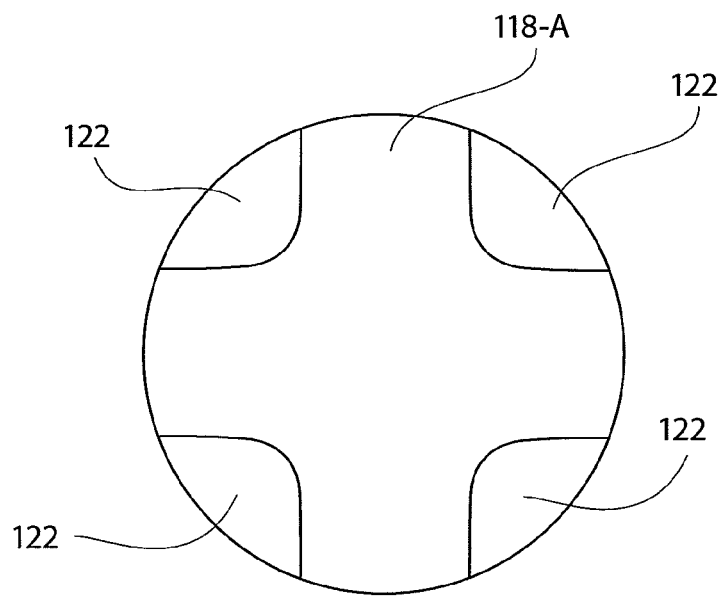
FIG. 14 is an end view showing an example of a four-prong filter.

As shown in FIGS. 9 and 10, central window 118-A allows light, such as a laser beam 120, to pass, as will be subsequently described in more detail. The window can extend any number of prongs of various geometries to the side of the chamber wall within filter plug 106 for support but does not require them. FIGS. 11 through 14 show filter designs that range from zero prongs (annular) to four prongs. More specifically, FIG. 11 shows window 118-B having zero prongs, FIG. 12 shows window 118-C having two prongs, FIG. 13 shows window 118-D having three prongs, and FIG. 14 shows window 118-A having four prongs. Further configurations, such as a window with a single prong (not shown) may be used. If the window contains support prongs, then an air-permeable, blood-impermeable material 122 such as cotton can be pressed in between the prongs. In some embodiments, such as shown in FIG. 11, the window 118-B does not have prongs but is adhered to an annulus of air-permeable, blood-impermeable material 122 that may be attached to or wedged between the walls of the filter plug 106 or needle holder chamber. In some embodiments, acrylic may be used as the central window 118 and cotton may be used as the filter material 122, but other suitable materials may be used instead of or in conjunction with these materials.

Figure 15:
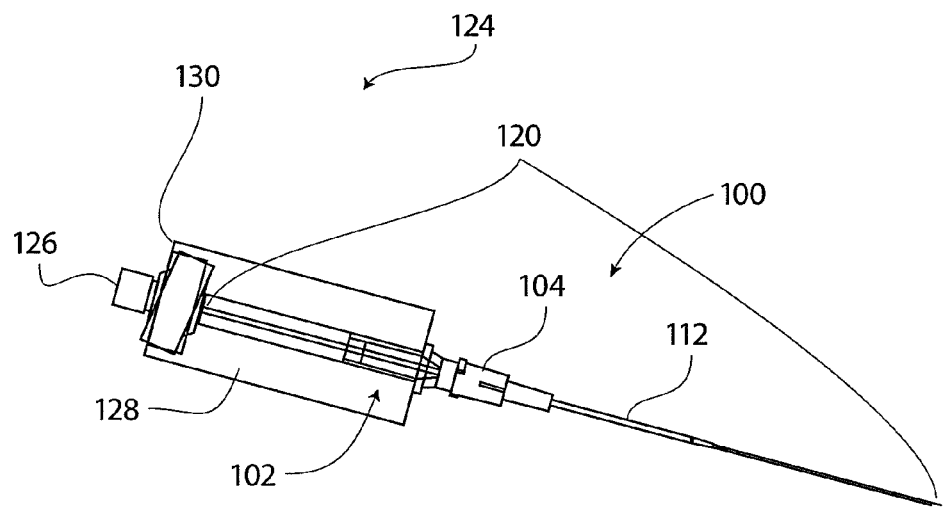
FIG. 15 is a perspective view showing an exemplary light emitting assembly attached to a catheter assembly.
Figure 16:
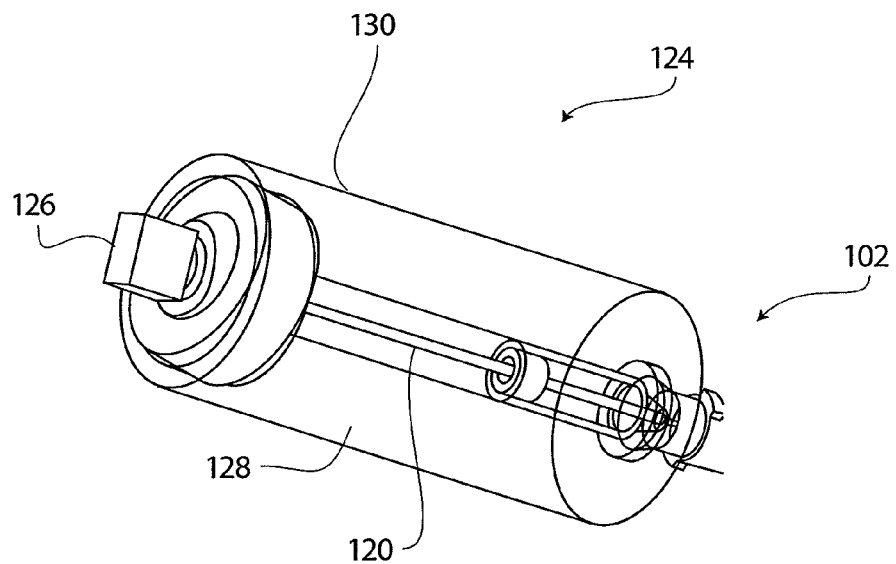
FIG. 16 is an enlarged perspective view showing the exemplary light emitting assembly of FIG. 15.

Referring to FIGS. 15 and 16, a light emitting assembly 124 is shown, mounted to needle/catheter assembly 100. In this exemplary embodiment, a light source such as a laser 126 is pivotably mounted to the proximal end of housing 128 with a spherical bearing 130 to allow the orientation of laser beam 120 to be adjusted. The proximal end of needle assembly 102 is removably received within the distal end of housing, such as with a friction fit, as best seen in FIG. 15. A central longitudinal bore extends through housing 128 to allow laser beam 120 to travel down the housing bore, through filter window 118 (such as window 118-A shown in FIGS. 9, 10 and 14), through needle holder 110 and needle 108, such that a coherent beam of light is projected from the distal tip of needle 108 in alignment with the needle. This arrangement allows a light dot to appear on the proposed needle insertion site of the patient to assist the medical practitioner in aligning the needle for insertion while still at a safe distance, as previously described.

Figure 17:
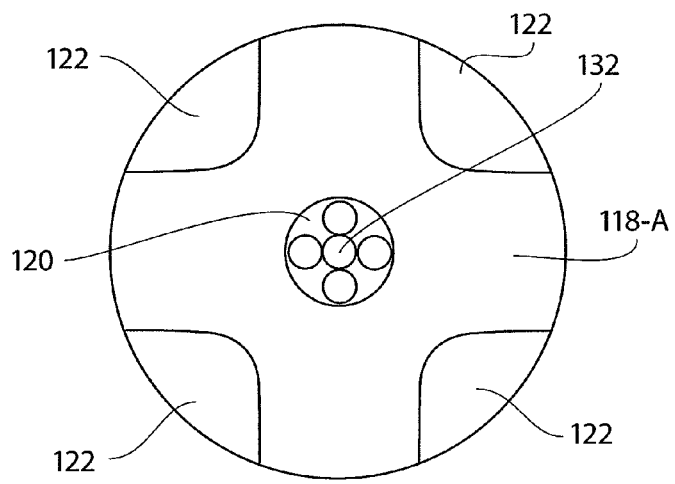
FIG. 17 is an end view schematically showing laser alignment with respect to the exemplary four-prong filter and needle bore.

Referring now to FIG. 17, alignment of laser beam 120 with respect to the bore 132 of needle 108 will be discussed. Relying only on precise dimensional tolerances of the components of the needle assembly 102 and light emitting assembly 124 to ensure that laser beam 120 is aligned with the needle bore 132 can be expensive. Instead, the exemplary embodiment described utilizes two design elements that provide low-cost, easy alignment. First, to align laser beam 120 in translation, a laser 126 having a beam 120 width that is significantly larger than the inner diameter 132 of the needle, as shown in FIG. 17. In this manner, there can be significant misalignment in translation, and the overlap between the larger laser beam 120 and the smaller needle bore 132 will still allow light to pass down the bore 132. Second, laser 126 may be mounted on a spherical bearing 130, as shown in FIGS. 15 and 16, to provide for rotational alignment. In some embodiments, spherical bearing 130 has a nylon sleeve between the bearing housing and the spherical race so that there is a moderate amount of friction maintaining the desired orientation of the laser. The laser 126 can typically be aligned rotationally in less than a minute by rotating the spherical bearing 130 with one's fingers while centering the bright glow of the laser in the flash-chamber visually. The four off-center circles depicted within laser beam 120 in FIG. 17 represent possible alternative positions of needle bore 132 with some degree of translational and/or rotational misalignment, but still allow laser beam 120 to successfully shine down the needle bore. In other embodiments, laser 126 or other light source may be permanently or adjustably aligned by other means during manufacture or in the field.

If the laser is used only to help a practitioner aim the needle with the naked eye, then using a visible laser is best. If the laser is used to help a practitioner or robot aim the needle while the vessels are illuminated with infrared light, then either a visible or IR laser could be used, depending on the exact setup. Using a visible laser with IR vessel illumination would help to disambiguate the light sources by toggling the camera between viewing IR and visible light. Using an IR laser with IR vessel illumination may be simpler in terms of camera setup but could possibly make it harder to see a distinct laser dot.

In some embodiments, a 5 mW focused laser diode is used, emitting a wavelength of 650 nm (red). In one embodiment, a 20 gauge IV catheter needle assembly is used, resulting in a targeting spot of the laser beam coming through the needle and onto the skin with a diameter of approximately 0.45 mm.

In other embodiments (not shown), a non-coherent light source could be used instead of laser 126. Laser 126 or other light source may be located on or within light emitting assembly 124 as previously described, or may be located remotely and optically coupled to the light emitting assembly 124 or needle assembly 102 with a light pipe or fiber optics.

Figure 18:
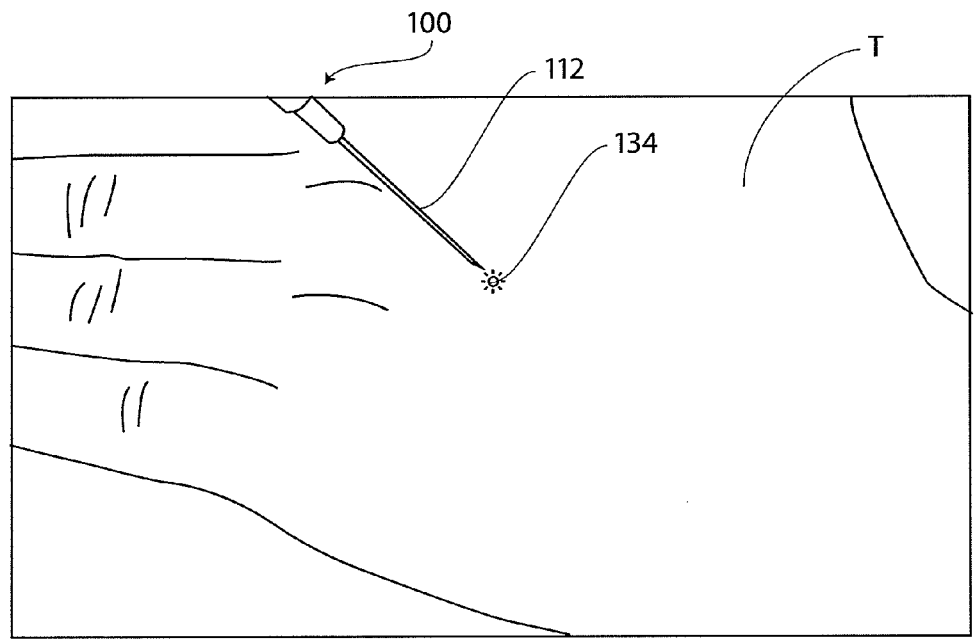
FIG. 18 is a perspective view showing the exemplary needle insertion assistance device shining a light dot on a hand.

As shown in FIG. 18, needle/catheter assembly 100, attached to light emitting assembly 124 as shown in FIG. 15, may be pointed towards target tissue T, such as on a hand, to create a light dot 134 on the tissue for assistance with pre-insertion alignment.

Figure 19:
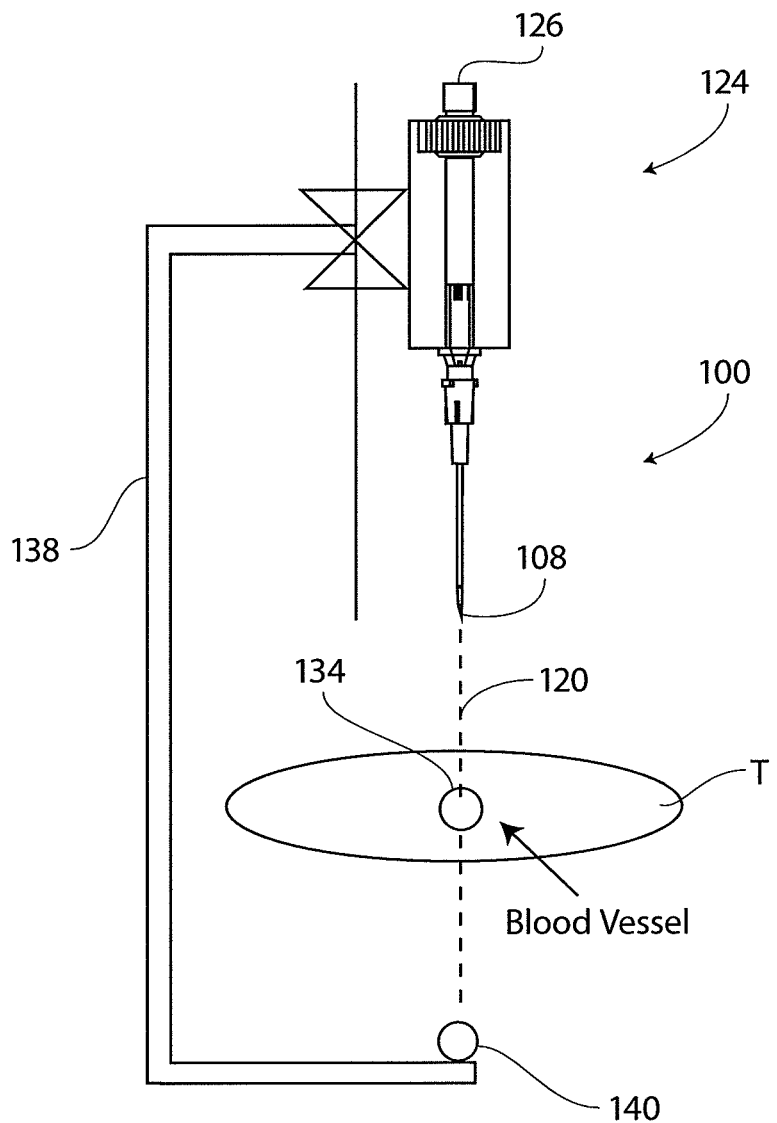
FIG. 19 is a schematic view showing an exemplary needle insertion assistance system which includes an alignment device mounted to a C-arm with a linear slide.

As schematically shown in FIG. 19, the laser/needle assembly 124/100 can be mounted on a prismatic, or linear, stage 136 that is aligned axially with the needle 108 such that translating along the stage will insert the needle in a straight line going through the projected insertion point. The stage 136 can be moved manually or actuated via a motor. As also depicted in FIG. 19, the laser/needle/linear-stage assembly 124/100/136 can be mounted on a C-arm 138 such that the needle 108 is held on one side of tissue T, and a light-detector 140 is held on the opposite side of that tissue. By moving the C-arm device 138 and beaming an IR laser through the stationary tissue T, one could use the light-detector signal to align the linear stage mounted assembly for insertion directly in-line with a blood vessel. One embodiment would be intended for IV insertions in the hand and arm such that the hand or arm is placed in the middle of C-arm 138 to detect veins. Another embodiment is intended for arterial lines such that the wrist is placed in the middle of C-arm 138 to detect arteries. In some embodiments, C-arm device 138, linear stage 136 and light emitting assembly 124 are configured as durable equipment that may be sterilized and reused, while needle assembly 102 and catheter assembly 104 are configured to be single-use disposable devices. According to some method embodiments, the devices disclosed herein may be used to access target tissue other than veins or arteries to extract or introduce blood or other fluid(s).

What is claimed is:

1. A visual-aid device for vascular needle insertion comprising:
    a needle having a proximal end, a sharp distal end, and a lumen extending between the proximal and distal ends;
    a flexible catheter having a lumen configured to receive the distal end of the needle therethrough;
    a flash chamber located at the proximal end of the needle and in fluid communication with the needle lumen, the flash chamber comprising a non-opaque portion configured to permit visualization of a body fluid located inside the chamber from outside of the chamber;
    a filter attached to the flash chamber and having a proximal side and a distal side, the distal side being located in fluid communication with the inside of the flash chamber and the proximal side being located in fluid communication with the outside of the flash chamber, the filter being configured to allow air to pass therethrough and to prevent or inhibit liquid from passing therethrough; and
    a light emitting assembly having an output optically coupled to the needle such that light from the light emitting assembly can travel from the proximal end of the needle through the distal end of the needle to project a visible spot on an object adjacent to the distal end of the needle when the filter is attached to the flash chamber.

2. The visual-aid device of claim 1, further comprising a filter assembly that includes the filter, wherein the needle lumen has a central longitudinal axis and the filter assembly lies on a projection of the central longitudinal axis.

3. The visual-aid device of claim 2, wherein the filter assembly comprises an optically transparent or translucent center portion that lies on the axis projection and an opaque filter portion that lies off of the axis projection.

4. The visual-aid device of claim 3, wherein the filter assembly is configured as removable plug insertable into a proximal end the flash chamber.

5. The visual-aid device of claim 3, wherein the center portion of the filter assembly includes at least one prong that extends radially outward.

6. The visual-aid device of claim 3, wherein the center portion comprises acrylic and the filter comprises cotton.

7. The visual-aid device of claim 1, wherein the light emitting assembly comprises a laser removably affixed to a proximal end of the flash chamber.

8. The visual-aid device of claim 1, wherein the light emitting assembly is configured as a reusable component, and the needle, the flash chamber and the filter are configured as a single disposable component.

9. A method of visually assisting with insertion of a vascular needle into a body of a mammal, the method comprising:
    providing a needle assembly having a needle with a proximal end, a sharp distal end, and a lumen extending between the proximal and distal ends, the needle assembly further comprising a flash chamber located at the proximal end of the needle, the flash chamber comprising a filter;
    inserting the distal end of the needle through a lumen of a flexible catheter;
    optically coupling an output of a light emitting assembly to the needle such that light from the light emitting assembly travels from the proximal end of the needle through the distal end of the needle;
    positioning the needle adjacent to the mammal so that light emitted from the distal end of the needle projects onto the mammal and creates a visible spot of light;
    moving the spot of light to a desired venipuncture location;
    inserting the distal end of the needle and a distal end of the catheter into a vein of the mammal;
    allowing air to escape from the needle lumen through the filter and allowing the filter to prevent or inhibit blood from passing therethrough;
    observing blood filling the flash chamber located at the proximal end of the needle;
    removing the needle from the catheter and the patient while leaving the distal end of the catheter in the vein.

10. The method of claim 9, wherein the flash chamber is in fluid communication with the needle lumen, the flash chamber comprising a non-opaque portion configured to permit visualization of a body fluid located inside the chamber from outside of the chamber, the flash chamber further comprising a filter having a proximal side and a distal side, the distal side being located in fluid communication with the inside of the flash chamber and the proximal side being located in fluid communication with the outside of the flash chamber, the filter being configured to allow air to pass therethrough and to prevent or inhibit blood from passing therethrough.

11. The method of claim 10, wherein the needle assembly comprises a filter assembly that includes the filter, wherein the needle lumen has a central longitudinal axis and the filter assembly lies on a projection of the central longitudinal axis.

12. The method of claim 11, wherein the filter assembly comprises an optically transparent or translucent center portion that lies on the axis projection and an opaque filter portion that lies off of the axis projection.

13. The method of claim 12, wherein the filter assembly is configured as a removable plug insertable into a proximal end the flash chamber.

14. The method of claim 12, wherein the center portion of the filter assembly includes at least one prong that extends radially outward.

15. The method of claim 12, wherein the center portion comprises acrylic and the filter comprises cotton.

16. The method of claim 9, wherein the light emitting assembly comprises a laser removably affixed to a proximal end of the flash chamber.

17. The method of claim 16, further comprising removing the laser from the proximal end of the flash chamber and reusing the laser by subsequently attaching it to a proximal end of another flash chamber.

18. The method of claim 10, wherein the light emitting assembly is configured as a reusable component, and the needle, the flash chamber and the filter are configured as a single disposable component.

* * * * *